(12) United States Patent  
Swanson

(10) Patent No.: US 6,368,147 B1  
(45) Date of Patent: Apr. 9, 2002

(54) ZERO INSERTION FORCE PERCUTANEOUS CONNECTOR AND FLEXIBLE BRAIN PROBE ASSEMBLY

(75) Inventor: John W. Swanson, Portland, OR (US)

(73) Assignee: MicroHelix, Inc., Portland, OR (US)

( * ) Notice: Subject to any disclaimer, the term of this patent is extended or adjusted under 35 U.S.C. 154(b) by 0 days.

(21) Appl. No.: 09/518,006

(22) Filed: Mar. 2, 2000

(51) Int. Cl.$^7$ .............................................. H01R 12/24
(52) U.S. Cl. ...................................... 439/496; 600/378
(58) Field of Search .............................. 439/496, 495, 439/909; 607/116, 148; 600/393, 372, 378, 394

(56) References Cited

U.S. PATENT DOCUMENTS

| | | | |
|---|---|---|---|
| 3,154,365 A | * 10/1964 | Crimmins | 439/633 |
| 3,995,644 A | * 12/1976 | Parsons | 439/909 |
| 4,684,183 A | * 8/1987 | Kinoshita et al. | 439/77 |
| 5,304,214 A | * 4/1994 | DeFord et al. | 607/105 |
| 5,383,788 A | * 1/1995 | Spencer | 439/67 |
| 5,403,202 A | * 4/1995 | Roehling | 439/496 |
| 5,496,182 A | * 3/1996 | Yasumura | 439/62 |
| 5,573,551 A | * 11/1996 | Lin et al. | 607/33 |
| 5,604,976 A | * 2/1997 | Stobie et al. | 29/825 |
| 6,086,412 A | * 7/2000 | Watt et al. | 439/496 |

* cited by examiner

*Primary Examiner*—Brian Sircus  
*Assistant Examiner*—Javaid Nasri  
(74) *Attorney, Agent, or Firm*—Timothy E. Siegel

(57) ABSTRACT

A percutaneous connector comprises a female-half that includes a housing that has a pair of side walls, each having an interior surface. An electrical contact assembly is arranged along the interior surface of at least one of the side walls and has a set of first electrical contacts. Insulating material electrically isolates the electrical contacts from one another. In addition, an electrical conductor attached to each electrical contact extends outside of the housing. A male-half includes a sheet of resilient material, bent into a U-shape and having two opposed outer surfaces. A handle assembly is adapted to permit a user to squeeze the two opposed outer surfaces closer to each other. In addition, a set of second contacts is attached to at least one of the outer surfaces and is arranged in matching configuration to the first set of contacts. Insulating material electrically isolates the contacts from one another. With this design, a user can grasp the male-half by the handle assembly, squeeze together the two outer surfaces, place the male-half in the female-half and release the handle assembly so that the male set of contacts touches the female set of contacts. Additionally, a method of producing an electrode probe assembly, comprising, providing a flexible polymer substrate bearing a conductive material plating and using photolithography and electroplating to form a set of contacts and conductors on the flexible polymer substrate.

6 Claims, 3 Drawing Sheets

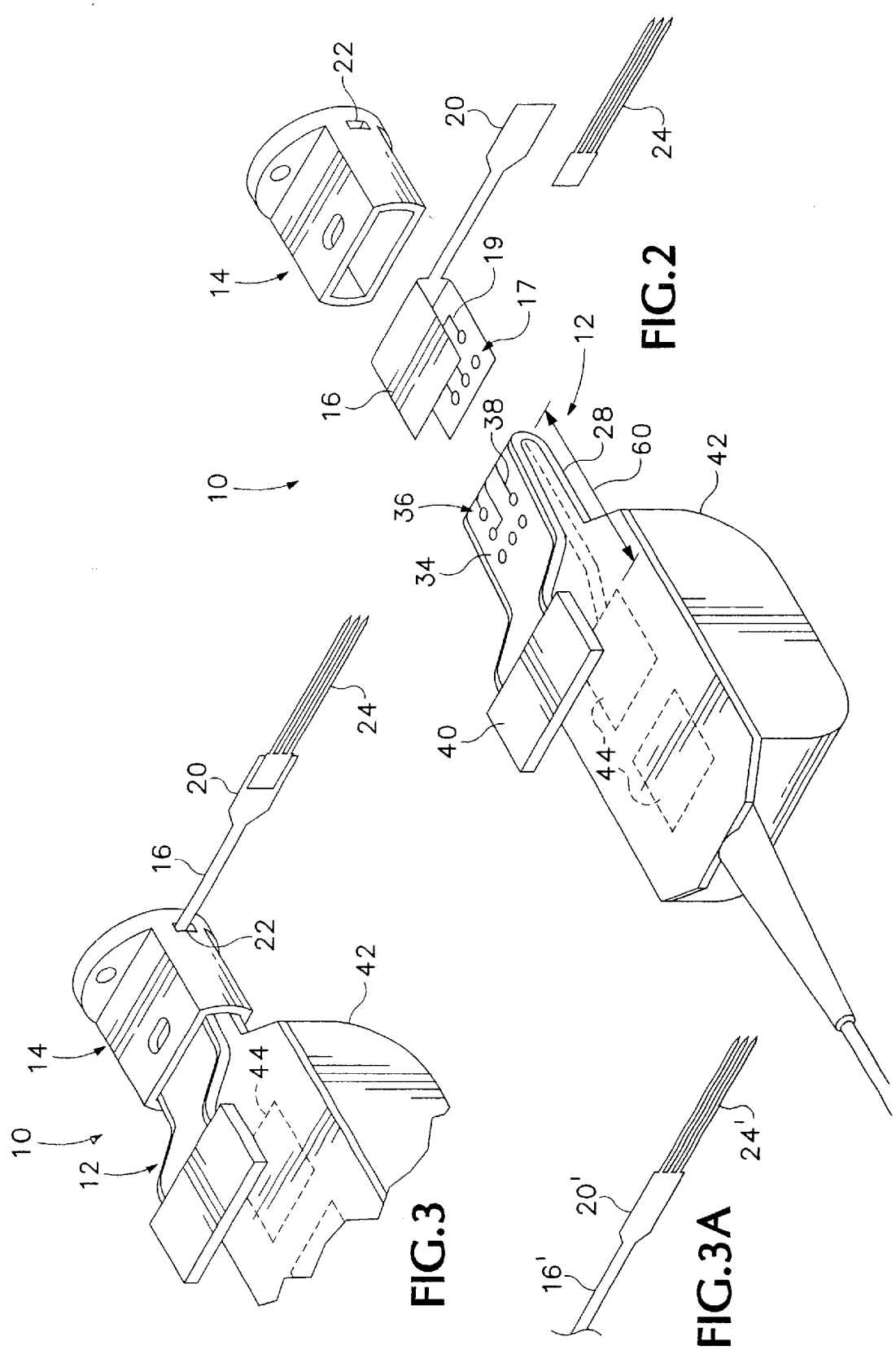

ZERO INSERTION FORCE PERCUTANEOUS CONNECTOR AND FLEXIBLE BRAIN PROBE ASSEMBLY

STATEMENT OF GOVERNMENTAL SUPPORT

This invention was made with government support under 2R44NS33427 awarded by SBIR. The Government has certain rights in the invention.

BACKGROUND OF THE INVENTION

The present invention is a zero insertion force percutaneous connector and a flexible brain probe assembly.

Fitting a probe assembly for measuring electrical activity of a mammalian test subject or patient's brain is a challenging operation. A problem is encountered in fitting the subject with a percutaneous connector assembly (a connector assembly having an in vivo connector half that extends through the skin) that does not unduly cause pain or creates a risk of infection. Complicating this task is he necessity of passing many different signal conductors through the percutaneous connector, a requirement that has significantly increased the size of the typical percutaneous connector.

Also, the in vivo connector half generally mates with an ex vivo connector half that routs the signals created by the connector to a destination, such as a piece of test equipment. Each time this cable is connected, some force must typically be applied to create the connection. As the site of the percutaneous connector may be quite tender, this generally causes pain or pressure to the subject. In a separate consideration, it is highly desirable to amplify the signals produced by the brain as closely as possible to the signal origin.

Creating the probe that contacts the brain tissue also represents a challenge to researchers. Researchers typically wish to measure electrical activity at specific sites within the brain that share a well-defined physical relationship to one another. Probes produced by photolithographic techniques, such as the probe designed by personnel at the University of Michigan that is known in the industry and research community as the "University of Michigan Probe," permit the accurate placement of electrode sites that are sufficiently small to permit the measurement of electrical activity at a specific set of predefined sites within the brain. Unfortunately, the desire to use photolithography has prompted the use of silicon as a substrate. Because this material is quite brittle, the use of it creates a risk of breakage inside the brain, endangering the subject or patient and limiting the insertion strategies available to researchers. Moreover, the use of silicon prevents the University of Michigan probe from moving with the brain, which does move about slightly within the skull. In addition, silicon is subject to some restoring force, which tends to cause a silicon probe to migrate over time. Both of these drawbacks have the potential result of causing trauma to the brain tissue.

Another type of probe that is currently available includes a set of insulated wires having laser created apertures exposing electrode sites. Although this type of probe is useful for many applications, it does not yield the precision or the freedom of electrode placement that the University of Michigan probe permits.

What is needed but not yet available is an electrode probe and method of making the same that affords unconstrained and accurate placement of the electrodes, but offers flexibility and robustness and is thereby less susceptible to breakage than currently available probes.

Also needed but not yet available is a percutaneous connector wherein the male-half can be inserted into the female-half without exerting pressure against the female-half, thereby avoiding the pain and/or tissue trauma that the insertion operation currently causes to patients and test subjects. In addition, a percutaneous connector is needed that brings a set of op-amps closer to the site where the signals exit the body than has heretofore been possible.

SUMMARY

In a first separate aspect, the present invention is a percutaneous connector. It comprises a female-half including a housing having a pair of side walls, each having an interior surface. An electrical contact assembly is arranged along the interior surface of at least one of the side walls and has a set of first electrical contacts. Insulating material electrically isolates the electrical contacts from one another. In addition, an electrical conductor attached to each electrical contact extends outside of the housing. A male-half includes a sheet of resilient material, bent into a U-shape and having two opposed outer surfaces. A handle assembly is adapted to permit a user to squeeze the two opposed outer surfaces closer to each other. In addition a set of second contacts is attached to at least one of the outer surfaces and is arranged in matching configuration to the first set of contacts. Insulating material electrically isolates the contacts from one another. With this design, a user can grasp the male-half by the handle assembly, squeeze together the two outer surfaces, place the male-half in the female-half and release the handle assembly so that the male set of contacts touches the female set of contacts.

In a second separate aspect, the present invention is a connector assembly for connecting a set of first conductors to a set of second conductors that includes a first half and a second half that mates to the first half. The first half includes a substrate of resiliently compressible, insulating material, which supports a set of first contacts, each connected to a the first conductor. In addition, the substrate of resiliently compressible, insulating material defines a set of isolation cuts, each disposed about one of the first contacts and detaching the substrate of resiliently compressible, insulating material inside of the isolation cut from the substrate of material outside of the isolation cut. The second half of the connector assembly comprises an insulating substrate and a set of second contacts, each connected to the second conductor and supported by the insulating substrate, and positioned in matching arrangement to the set of first contacts. A connective bracket assembly is adapted to hold the first set of contacts in contact to the second set of contacts.

In a third additional separate aspect, the present invention is a method of producing an electrode probe assembly, comprising, providing a flexible polymer substrate bearing a coating of conductive material and using photolithography and electroplating to form a set of contacts and conductors on the flexible polymer substrate.

In a forth additional separate aspect, the present invention is a percutaneous connector comprising a first half and a mating second half. The first half is adapted to be set into the body of a patient and includes an array of first contacts having a density of greater than 25 contacts per $cm^2$. The second half is adapted to mate with the first half and includes an array of second contacts positioned in mating conformity with the set of first contacts and further including a set of op-amps, each connected to one of the second contacts and positioned within 2 cm that second contact.

The foregoing and other objectives, features and advantages of the invention will be more readily understood upon consideration of the following detailed description of the preferred embodiment(s), taken in conjunction with the accompanying drawings.

BRIEF DESCRIPTION OF THE DRAWINGS

FIG. 2 is an exploded perspective view of a connector according to the present invention.

FIG. 3 is a perspective view of the connector of FIG. 1, with the two connector halves mated.

FIG. 3A is a perspective of a portion of an alternative embodiment to FIG. 1, showing the differing structure of the alternative embodiment.

DETAILED DESCRIPTION OF THE PREFERRED EMBODIMENT

Figure 1:
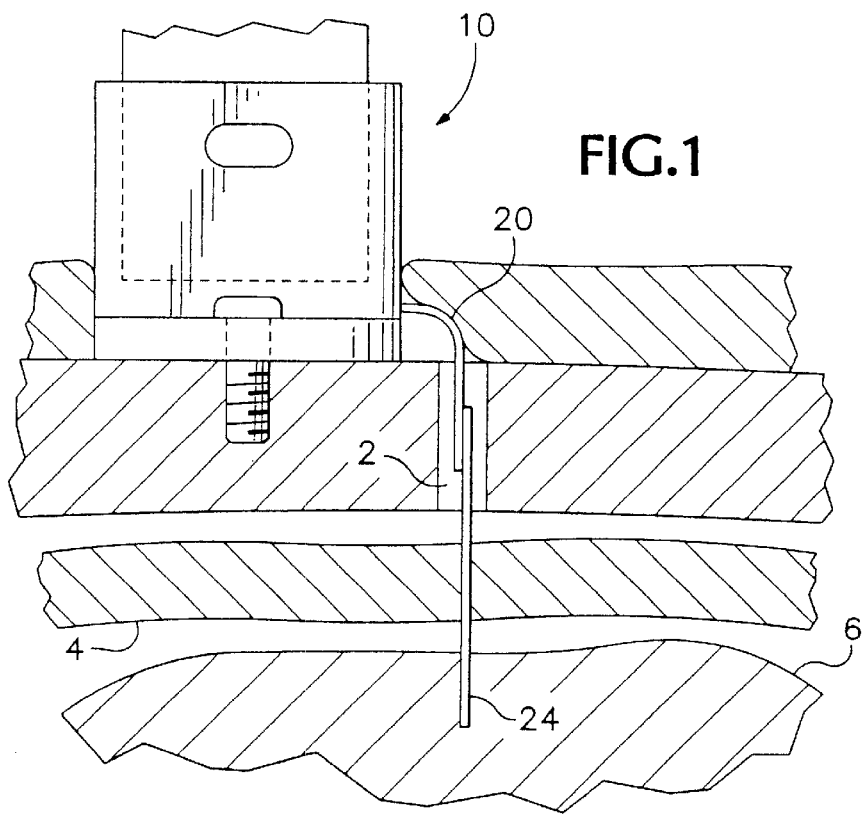
FIG. 1 is a side view of a connector and brain probe assembly according to the present invention, with the connector portion attached to the skull and the brain probe portion embedded in brain tissue.
Figure 4:
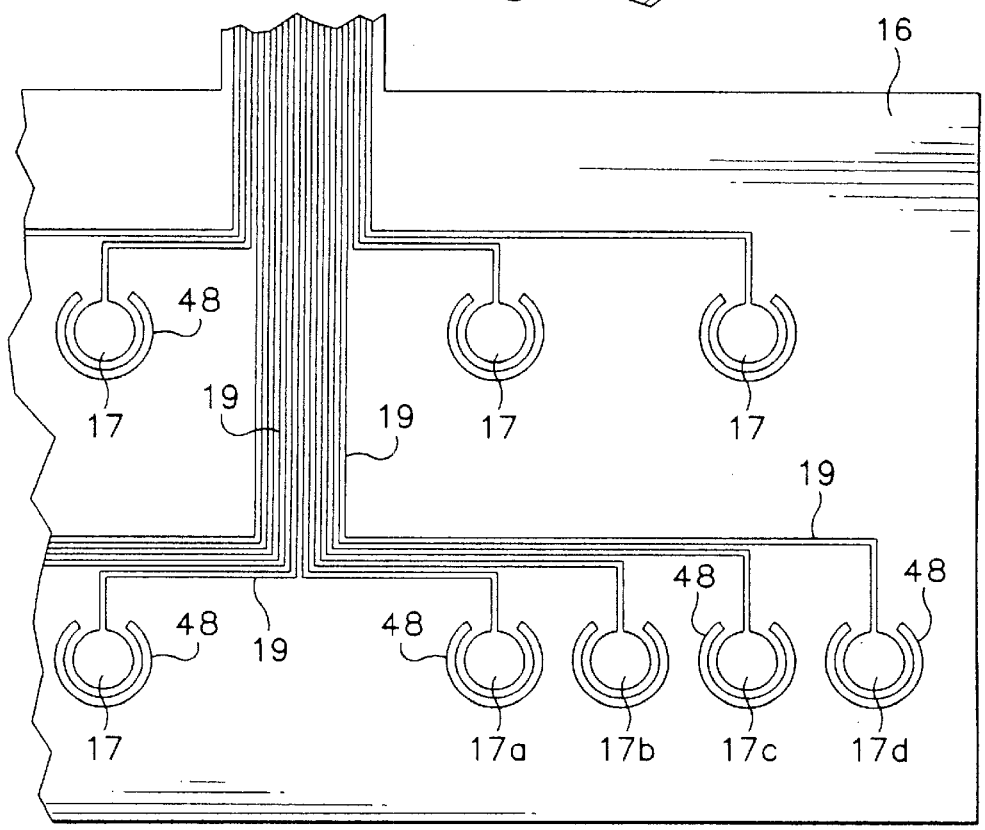
FIG. 4 is a greatly expanded plan view of a connective surface of the connector of FIG. 1.

Referring to FIG. 1, a percutaneous connector 10 is screwed into the skull 1 and is connected, by way of a multi-conductor microcable 20, to a brain probe 24 that passes through an aperture 2 in the skull, through the dura 4 (and into the brain 6), for measuring brain activity at a specific set of points.

Referring to FIGS. 2, 3 and 3A a percutaneous connector 10 according to the present invention includes a male-half 12, a female-half bracket 14 and a female-half flex circuit (or flexible polymer) connective assembly 16 bearing a set of contacts 17 and conductive traces 19. A multi-conductor microcable 20 forms a portion of assembly 16 and is threaded through an aperture 22 in bracket 14. The microcable 20 attaches to and extends traces 19 to brain probe 24. As shown in FIG. 3a in an alternative embodiment, a connective assembly 16' includes a microcable 20' that includes a brain probe 24' as a unitary part of its construction. The male-half includes a resilient clip portion 28, the exterior of which is covered with a flex-circuit 34 bearing a set of contacts 36 (matching the arrangement of contacts 19) and conductive traces 38.

A first prong 40 and a second prong 42, which is physically coincident with an op-amp housing, partially defines clip portion 28. A user can grasp male-half 12 by the first and second prongs 40 and 42 to squeeze these prongs 40 and 42 together. The male-half 12 can then be inserted into the female-half 14, without exerting pressure against female-half 14, which could cause pain or tissue trauma to the patient or test subject. Finally, the user releases prongs 40 and 42 so that the resiliency of clip 28 will force each exterior side of clip 28, and therefore contacts 36, to touch the contacts 17 in female-half 14.

Referring to FIG. 4 and 5a–5g, contacts 17 and traces 19 are made of conductive material, such as a metal (copper, gold or sliver) or a conductive polymer that has been deposited and etched on top of a laminate having a layer of dielectric substrate 50 and a base layer silicone 70 or some other biocompatible, compliant material. Semicircular isolation cuts 48 through the layers 50 and 70 (in an alternative preferred embodiment only layer 50 is cut through by the laser) positionally decouple a first contact 17a from neighboring contacts 17b, 17c and 17d, permitting contact 17a to be depressed into the spongy layer of silicone 70 without pulling down the neighboring contacts 17b, 17c and 17d. This independent depressability causes the protrusional misalignment of contacts 17 and 36 to be forgiven.

The miniature scale that is made possible by the use of photolithography and flex circuit technology, as described above, facilitates a further advantage that may be realized as part of the present invention. This is the placement of op amps in extremely close proximity to contacts 36. For connectors in which the contacts are spread apart from each other, it is necessary to gather together conductive paths from all the different contacts prior to sending them all to a set of op amps. Because contacts 36 are all so close together, traces 38 are routed to a set of op amps 44, that are a distance 60 from the distal tip of clip portion 28. In a preferred embodiment, distance 60 is less than 0.5 cm, making the furthest distance between op amps 44 and any of the contacts 36 to be less than 1 cm. This short distance is made possible also by the fact that the op amps 44 are housed in the second prong 42, which doubles as an op amp housing. As a result, signal line noise and cross talk are minimized.

Figure 5A:
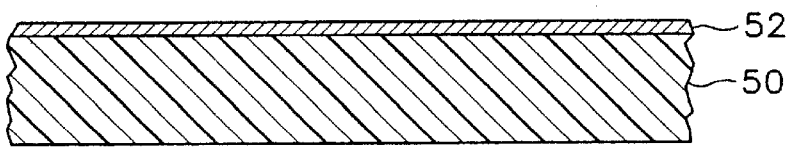
FIGS. 5a–5g is a series of greatly enlarged side cross-sectional views showing the construction of the connector flex circuit, or thin film, which may include the brain probe flex circuit of FIG. 1 in a single unit.
Figure 5B:
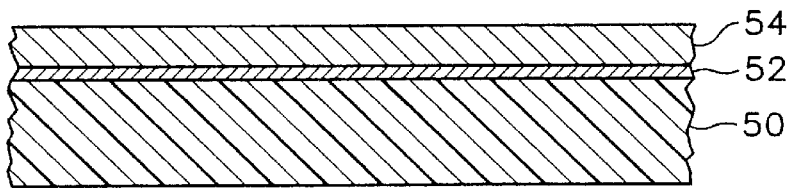
Figure 5C:
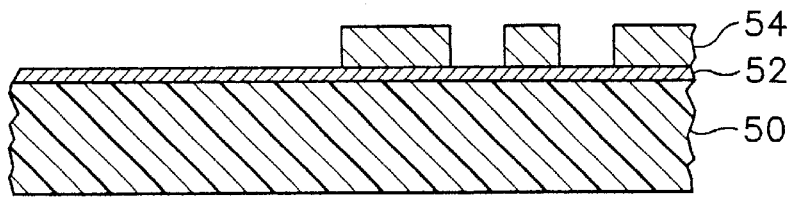
Figure 5D:
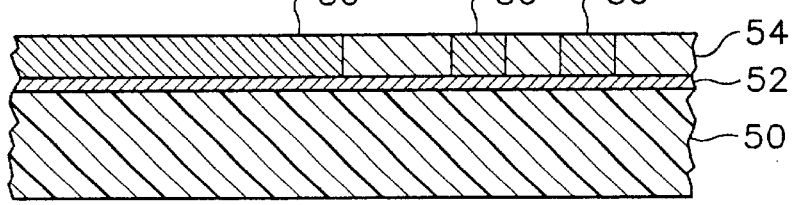
Figure 5E:
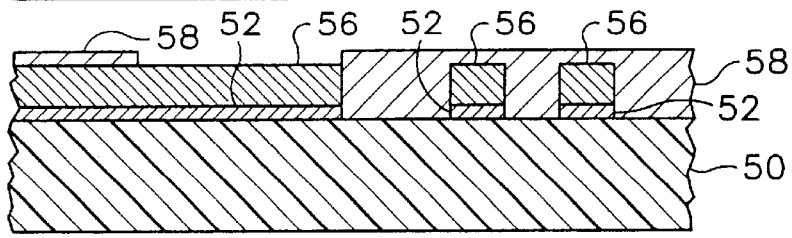
Figure 5F:
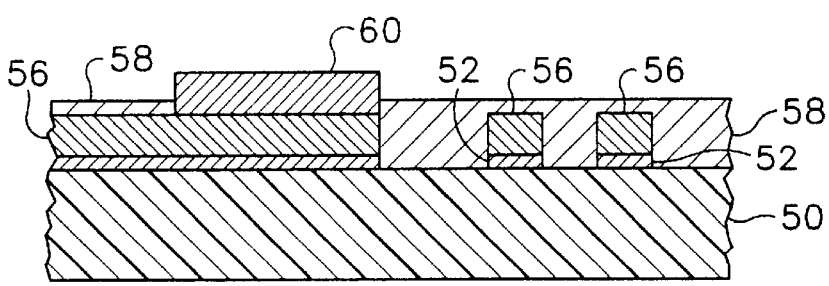
Figure 5G:
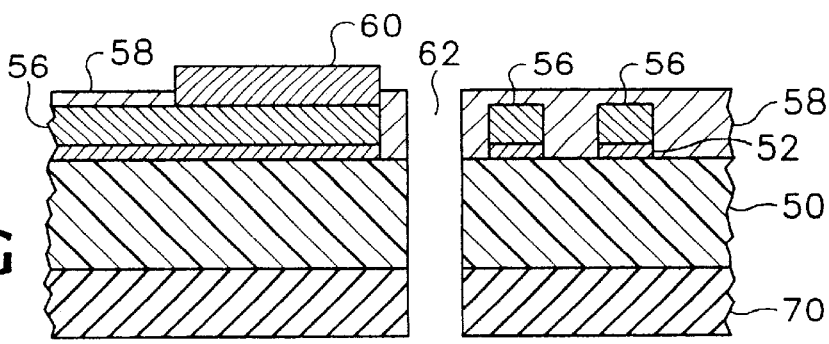

Referring to FIGS. 5a–5g, the photolithography process for making the brain probe 24 and the contacts of the percutaneous probe contact structure 30 are quite similar, except that different materials may be used and the percutaneous probe contact structure 30 includes a base layer of silicone 70, that is only shown in FIG. 5g, for the sake of simplicity. Referring specifically to FIG. 5a, the photolithography process begins with a layer of dielectric substrate 50, the composition of which is discussed below, that is coated with a base layer of conductive material 52, such as a titanium-gold-titanium sandwich. FIG. 5b shows the structure of FIG. 5a, which at this point has been covered with a layer of photo resist material 54, typically applied by spin-coating. FIG. 5c shows the effect of exposing the photo resist material to a pattern of light and washing off the exposed (or not exposed if a negative process is used) material with a developing agent. Next, as shown in FIG. 5d, additional conductive material (typically copper) is built up on the exposed base layer 52, typically through electrolysis. As shown in FIG. 5e, the remaining photo resist material 54 is washed off with a solvent and a layer of dielectric (and permanent) photo resist 58 is applied and patterned, via exposure to a pattern of light and subsequent washing with a developing agent or solvent. Then, additional electrolytic plating is performed (FIG. 5f) to create a contact 60 and the substrate is cut with an nd:YAG laser to form a kerf or cut 62. When the process shown in FIGS. 5a–5g is for producing connector 10, cut 62 is the same as isolation cut 48. When the process shown in FIGS. 5a–5g is for producing a brain probe 24, cut 62 separates a first brain probe 24 from a wafer or thin plastic film upon which several brain probes have been etched. In contrast to the situation with respect to silicon, which may be separated by etching, it appears that no etching process has been developed for cutting the materials used for substrate 50, which are discussed below.

The dielectric substrate 50 that is used for the brain probe 24 is preferably a polymer material having a high glass transition temperature, high tensile strength and low elasticity. More specifically, substrate 50 may be made of polyether sulfone, polyimide or other material having the desired characteristics. If polyimide is used, it should be coated or treated so that it does not dissolve in the body's interstitial fluid, or used for a probe that is not to be implanted for long enough for the polyimide to dissolve.

Photo resist material 54 may be a photosensitive acrylate, polyether or polyurethane, preferably having a high molecular weight. Permanent photo resist 58 may be a permanent polyimide, a type of material that is widely available from well-known photo resist companies. These companies typically sell a wet etch agent specifically designed to etch each permanent polyimide photo resist that they sell.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A high-density connector assembly for connecting a set of first conductors to a set of second conductors, comprising:
   a) a first half, including:
      i) a laminated substrate comprising a first layer of dimensionally stable dielectric material, an underlying layer of resiliently compressible, material and a layer of substantially rigid material underlying said layer of resiliently compressible material;
      ii) a set of at last fifteen first contacts, having a density of greater than 25 contacts per square centimeter, each connected to one of said set of first conductors and supported by said laminated substrate, a first pain of said first contacts being spaced apart in a first dimension and a second pair of said first contacts being spaced apart in a second dimension, which is different from said first dimension; and
      iii) wherein said laminated substrate defines a set of isolation cuts, each isolation cut disposed about one of said first contacts and substantially detaching said layer of dimensionally stable dielectric material inside of said isolation cut from said layer of dimensionally stable dielectric material outside of said isolation cut;
   b) a second half comprising:
      i) an insulating substrate; and
      ii) a set of second contacts, each connected to one of said set of second conductors and supported by said insulating substrate, and positioned in matching arrangement lo said set of first contacts; and
   c) a connective bracket assembly adapted to hold said set of first contacts in direct contact to said set of second contacts.

2. The connector of claim 1 wherein said set of first contacts is arranged in a two dimensional pattern.

3. The connector of claim 1 wherein said layer of dimensionally stable dielectric material is made of polyether sulfone.

4. The connector of claim 1 wherein said layer of dimensionally stable dielectric material is made of polyimide.

5. The connector of claim 1 wherein said resiliently compressible material is made of silicone.

6. The connector of claim 1 wherein said isolation cuts extend entirely through said layer of dimensionally stable dielectric material but not through said layer of resiliently compressible material.

* * * * *

UNITED STATES PATENT AND TRADEMARK OFFICE
CERTIFICATE OF CORRECTION

PATENT NO.     : 6,368,147 B1
DATED          : April 9, 2002
INVENTOR(S)    : John W. Swanson It is certified that error appears in the above-identified patent and that said Letters Patent is hereby corrected as shown below:

Column 1,
Line 19, change "he" to -- the --.

Column 5,
Line 28, change "pain" to -- pair --.

Column 6,
Line 13, change "lo" to -- to --.

Signed and Sealed this

Twenty-fourth Day of September, 2002

Attest:

JAMES E. ROGAN
Attesting Officer                Director of the United States Patent and Trademark Office